(12) United States Patent
Yang et al.

(10) Patent No.: US 7,691,966 B2
(45) Date of Patent: Apr. 6, 2010

(54) METHOD FOR QUANTITATIVE ANALYSIS FOR PROLYL HYDROXYLASE ACTIVITY USING FLUORESCENCE POLARIZATION

(75) Inventors: Eun Gyeong Yang, Seoul (KR); Hyun Ju Cho, Sacheon-si (KR); Hyunsung Park, Seongnam-si (KR)

(73) Assignee: Korea Institute of Science and Technology, Seoul (KR)

( * ) Notice: Subject to any disclaimer, the term of this patent is extended or adjusted under 35 U.S.C. 154(b) by 387 days.

(21) Appl. No.: 11/164,813

(22) Filed: Dec. 6, 2005

(65) Prior Publication Data

US 2007/0020718 A1    Jan. 25, 2007

(30) Foreign Application Priority Data

Jul. 22, 2005   (KR)   ................ 10-2005-0066881

(51) Int. Cl.
C07K 14/00    (2006.01)
C12Q 1/00     (2006.01)
C12Q 1/30     (2006.01)

(52) U.S. Cl. .................. 530/326; 530/300; 530/324; 530/325; 435/4; 435/7.1; 435/27

(58) Field of Classification Search .............. None
See application file for complete search history.

(56) References Cited

U.S. PATENT DOCUMENTS 6,566,088 B1 * 5/2003 McKnight et al. ............ 435/24
6,787,326 B1   9/2004 Ratcliffe et al.

FOREIGN PATENT DOCUMENTS

WO    WO 96/39426 A1 * 12/1996

OTHER PUBLICATIONS

NPL-GenBank Accession No. NP_000542, (named as NPL-NP000542), Accessed Jun. 5, 2008.*
NPL-GenBank Accession No. NP_937799, (named as NPL-NP937799), Accessed Jun. 5, 2008.*
ACP definition from www.chemimpex.com/category1.asp?cid=500-001-008&lvl=3, pp. 1-4. Accessed Sep. 15, 2008.*
Oehme et al., "A nonradioactive 96-well plate assay for the detection of hypoxia-inducible factor prolyl hydroxylase activity", Analytical Biochemistry (2004), 330: 74-80.
Yu et al., "Dynamic, Site-specific Interaction of Hypoxia-inducible Factor-1alpha with the von Hippel-Lindau Tumor Suppressor Protein", Cancer Research (2001), 61: 4136-4142.
Yu et al., "HIF-1alpha binding to VHL is regulated by stimulus-sensitive praline hydroxylation", PNAS (2001), 98(17): 9630-9635.
Min et al., "Structure of an HIF-1alpha-pVHL Complex: Hydroxyproline Recognition in Signaling", Science (2002), 296: 1886-1889.
Masson et al., "HIF prolyl and asparaginyl hydroxylases in the biological response to intracellular O2 levels", Journal of Cell Science (2003), 116: 3041-3049.
Hon et al., "Structural basis for the recognition of hydroxyproline in HIF-1alpha by pVHL", Nature (2002), 417 (27): 975-978.
Maxwell et al., "The tumour suppressor protein VHL targets hypoxia-inducible factors for oxygen-dependent proteolysis", Nature (1999), 399: 271-275.

* cited by examiner

*Primary Examiner*—Cecilia Tsang
*Assistant Examiner*—Julie Ha
(74) *Attorney, Agent, or Firm*—Joseph H. Kim; JHK Law

(57) ABSTRACT

The present invention relates to a method for analyzing the interaction between HIF-1 peptide and VBC protein using fluorescence polarization, more precisely, a method for quantitative analysis of formation of HIF-1-VBC protein complex which is composed of the steps of 1) preparing a fluorescent probe by attaching a fluorescein to hydroxyproline containing HIF-1 peptide; 2) reacting the fluorescent probe with VBC protein; and 3) measuring the fluorescence polarization of the above reactant and then comparing the fluorescence polarization with that of the fluorescent probe itself to investigate the changes of fluorescence polarization; a method for screening an inhibitor of the binding of HIF-1 peptide and VBC protein using the above method; and a method for analyzing the activity of prolyl hydroxylase using the above method. The method of the present invention enables simple analysis of the interaction between HIF-1 peptide and VBC protein by observing changes of fluorescence polarization and thus, it can be effectively used for high-speed screening using a well plate.

9 Claims, 10 Drawing Sheets

METHOD FOR QUANTITATIVE ANALYSIS FOR PROLYL HYDROXYLASE ACTIVITY USING FLUORESCENCE POLARIZATION

TECHNICAL FIELD

The present invention relates to a method for quantitative analysis of interaction between probe constructed by attaching fluorescein to hydroxyproline containing HIF-1 peptide and VBC protein using fluorescence polarization, a screening method for an inhibitor of the interaction based on the above method and an assay for the activity of prolyl hydroxylase also using the same.

BACKGROUND ART

HIF-1 (hypoxia inducible factor-1) is a protein that plays an important role in various cell responses in hypoxic condition including regulation of a gene involved in energy metabolism, vasomotor control, angiogenesis and apoptosis. In particular, HIF-1α (alpha) is degraded by proteosome under normoxic conditions, while being stabilized in hypoxic conditions. Such mechanism is regulated by the interaction between pVHL (von Hippel-Lindau tumor suppressor) protein and HIF-1α. The inhibition of the interaction between HIF-1α and pVHL results in the acceleration of cell cycle, angiogenesis and cell survival function in hypoxic condition, which provides an idea for the treatment of ischemia such as coronary insufficiency, cerebral insufficiency and vascular insufficiency (U.S. Pat. No. 6,787,326 B1). On the contrary, the promotion of the interaction results in the inhibition of angiogenesis in normoxic conditions, suggesting that tumors might be suppressed by that mechanism (Amato G. et al., *Nature Reviews* 2: 1-9, 2003).

The binding of VHL protein with human HIF-1α depends on hydroxyproline group residing in $402^{nd}$ or $564^{th}$ amino acid of human HIF-1α. And the interaction between VHL protein and HIF-1α is regulated by hydroxylation of a specific proline group of HIF-1α by prolyl hydroxylase (Masson N. and Ratcliffe P J., *Journal of Cell Science* 116: 3041-3049, 2003). Particularly, prolyl hydroxylase-2 uses oxygen, iron and 2-oxoglutarate as cofactors for its reaction, and at this time ascorbate is necessarily used to prevent rapid inactivation of the enzyme by self-oxidation (Ivan M. et al., *PNAS* 99(21): 13459-13464, 2002). The disclosure of a mechanism that regulates hydroxylation-induced transcription and proteolytic destruction can be helpful for the studies on pathological mechanisms.

VHL protein is composed of β domain containing about 100 amino acids and α domain containing approximately 35 amino acids. The β domain is bound to Elongin C protein to form a VHL-Elongin C complex and then Elongin B protein is bound to the position of Elongin C to form a VBC protein. To the rest α area of the VBC protein is bound to HIF-1α, during which hydrogen bonds between the $115^{th}$ His group and the $111^{th}$ Ser group of VHL protein and the $564^{th}$ hydroxy-Pro group of HIF-1α are crucial (Min J. H. et al., *Science* 296: 1886-1889, 2002).

The interaction between VHL protein and HIF-1α has been detected by biochemical or immunological approaches. First, two-hybrid assay has been used to detect the interaction between two different proteins. In this assay, DNA binding domain (DBD) of yeast GAL4 transcription factor is fused into VHL protein and transcriptional activation domain (TAD) is fused into HIF-1α, respectively, and then the transcription is activated by the binding of the two proteins. At this time, the activation of the transcription induced by the binding of the two different proteins is easily detected by using a reporter gene such as GFP (green fluorescent protein), luciferase and β-galactosidase. That is, upon the combination of VHL protein and HIF-1α, a reporter gene is activated, by which the interaction between heterologous proteins can be easily detected (U.S. Pat. No. 6,787,326 B1).

There is another method to detect the interaction between two proteins, in which either VHL protein or HIF-1α protein is labeled with detectable material and the remaining one is fixed in solid carrier. And the detectable marker is not limited as long as it can be inserted in a recombinant protein, which is exemplified by $^{35}S$-methionine, HA tag, GST tag, histidine tag, etc (U.S. Pat. No. 6,787,326 B1). In general, HIF-1α is labeled with GST tag and VHL protein is marked by $^{35}S$, and the interaction between the two proteins is observed by SDS-PAGE and autoradiography (Yu F. et al., *PNAS* 98(17): 9630-9635, 2001). However, this method has problems of requiring a large amount of samples, intricacy of the protocol, lengthy analysis time and the use of radioactive reagents.

Coimmunoprecipitation of VHL protein and a specific part of HIF-1α is a way to screen HIF-1α interacting with VHL protein (Yu F. et al., *Cancer Research* 61: 4136-4142, 2001). In addition, scintillation proximity assay can be also used to detect the interaction, in which a target compound is radiolabeled and scintillation occurring during the process of binding of two proteins is detected (U.S. Pat. No. 6,787,326 B1).

However, all these biochemical, immunological or radiographic assay present problems including intricacy of protocol and high costs. Therefore, an alternative assay which is easier and simpler is required to observe characteristics of the binding of VHL protein with HIF-1α. Accordingly, a method has been developed that analyzes the binding of VBC protein with HIF and characteristics of hydroxylation involved therein using a 96-well plate in a short period of time without using a radioactive agent (F. Oehme, et al., *Analytical Biochemistry* 330: 74-80, 2004). Precisely, the method is to quantify $OD_{450}$ of the complex of biotin labeled HIF-1α (biotinyl-HIF-1α) and VBC protein in a plate coated with avidin. This method enables the observation of hydroxylation of HIF at the concentration range of tens of nano mols and simple quantification, but still presents a problem of requirement of using an expensive avidin coated plate.

Thus, the present inventors have made every effort to develop an alternative assay for quantifying the interaction between HIF-1 peptide and VBC protein, and as a result, the inventors have developed a method for quantitative analysis of the interaction between probe prepared by attaching a fluorescein to hydroxyproline containing HIF-1 peptide and VBC protein using fluorescence polarization. The method of the invention does not require the separation of the binders, making the procedure simple and lowering the costs for analysis owing to the automation using a well-plate. Therefore, the developed assay can be very useful for the detection of an inhibitor of the interaction or for the analysis of the activity of prolyl hydroxylase mediating hydroxylation of HIF-1.

DISCLOSURE

[Technical Problem]

It is an object of the present invention to provide a method for quantitative analysis of the proline hydroxylation-induced interaction between HIF-1 peptide and VBC protein.

[Technical Solution]

To achieve the above object, the present invention provides a method for quantitative analysis of proline hydroxylation-induced interaction between HIF-1 peptide and VBC protein using fluorescence polarization.

The present invention also provides a method for screening an inhibitor of the binding of HIF-1 peptide with VBC protein based on the above analytical method of the invention.

The present invention further provides a method for analysis of the activity of prolyl hydroxylase using the above analytical method.

Hereinafter, the present invention is described in detail.

The present invention provides a method for quantitative analysis of the interaction between Hydroxyproline containing HIF-1 peptide and VBC protein using fluorescence polarization.

Preferably, the analytical method of the present invention comprises the following steps:

1) preparing a fluorescent probe by attaching a fluorescein to Hydroxyproline containing HIF-1 peptide;
2) reacting the fluorescent probe with VBC protein; and
3) measuring the fluorescence polarization of the above reactant and then comparing the fluorescence polarization with that of the fluorescent probe itself to investigate the changes of fluorescence polarization.

In step 1), a fluorescent probe was synthesized with the selection of a specific peptide specifically binding to VBC protein from amino acid sequence of HIF-1 protein. Then, a fluorescein was conjugated to the synthesized peptide with the N-terminal insertion of an aminocaproic acid (ACA) linker. A specific proline residue of the peptide was hydroxylated to let the fluorescent probe contain hydroxyproline group.

The fluorescein used for peptide labeling of the invention is selected from a group consisting of fluorescein carboxylic acid (FCA), fluorescein isothiocyanate (FITC), fluorescein thiourea (FTH), 7-acetoxycoumarin-3-yl, fluorescin-5-yl, fluorescin-6-yl, 2',7'-dichlorofluorescin-5-yl, 2',7'-dichlorofluorescin-6-yl, dihydrotetramethylrosamine-4-yl, tetramethylrhodamine-5-yl, tetramethylrhodamine-6-yl, 4,4-difluoro-5,7-dimethyl-4-bora-3$a$,4$a$-diaza-s-indacene-3-ethyl and 4,4-difluoro-5,7-diphenyl-4-bora-3$a$,4$a$-diaza-s-indacene-3-ethyl. The hydroxylation of a specific proline residue can be induced by the addition of hydroxylated pro line amino acid (HyP amino acid of Merck Co. was added during the synthesis).

In the preferred embodiments of the present invention, 556-575 a.a. region and 390-417 a.a. region of HIF-1 α amino acid sequence (GeneBank accession No. U22431) (SEQ ID NO:5') were selected to synthesize peptides having amino acid sequences of each. Aminocaprioc acid linker was conjugated to the N-terminal of the synthesized peptide and the opposite of the connected linker was tagged with FITC, resulting in the preparation of F-P564 peptide having 20 amino acids, represented by SEQ ID NO:1 and F-P402 having 28 amino acids, represented by SEQ ID NO:2. The 564$^{th}$ proline (the 9$^{th}$ amino acid of the peptide represented by SEQ ID NO:1) of F-P564 and the 402$^{nd}$ proline (the 13$^{th}$ amino acid of the peptide represented by SEQ ID NO:) of F-P402 were hydroxylated by the addition of hydroxyproline, resulting in the synthesis of peptides F-HyP564 and F-HyP402 each represented by SEQ ID NO:3 and SEQ ID NO:4.

In step 2), the flourescent probe prepared in above step 1) was reacted with VBC protein which can be synthesized by conventional genetic recombination techniques.

To synthesize VBC protein, β domain of VHL protein is bound to Elongin C protein, resulting in VHL-Elongin C complex. Then, Elongin C of the complex is bound to Elongin B, resulting in the VBC protein. VHL, Elongin C and Elongin B genes are described in GenBank (Accession Nos. NM000551 (SEQ ID NO:6), NM007108 (SEQ ID NO:7) and NM005648 (SEQ ID NO:8), respectively).

In a preferred embodiment of the present invention, expression vectors which respectively containing a nucleotide sequence encoding VHL protein, a nucleotide sequence encoding Elongin C protein and a nucleotide sequence encoding Elongin B protein were constructed, then proper host cells were transfected with those vectors. VHL, Elongin C and Elongin B proteins were co-expressed as a complex in the host cells, followed by separation of the complex. VBC protein expressed in the host cells could be separated and purified from culture cells or culture fluid. The separation and purification of VBC protein can be carried out by one of conventional methods exemplified by dialysis, ultrafiltration, gel filtration and SDS-PAGE, which use the difference of molecular weights, ion-exchange column chromatography using the difference of electric charges, and high performance liquid chromatography using the difference of hydrophobicities.

The fluorescent probe-labeled peptide and VBC protein were mixed in a proper buffer solution at 25° C. at the ratio of 1:1-1:14 to induce the interaction between HIF-1 peptide and VBC protein.

In step 3), upon completion of the reaction, fluorescence polarization of the reactant of step 2) was measured by using fluorescent polarimeter. The obtained fluorescence polarization value was compared with that of the fluorescent probe itself, and the difference was recorded. The fluorescence polarization value of the fluorescent probe (a fluorescein-attached HIF-1 peptide) was comparatively low, but once the probe was bound to VBC protein having high molecular weight, the fluorescence polarization was greatly increased. The above result indicates that if there is no big difference in fluorescence polarization values upon the addition of VBC protein to the fluorescent probe, it means there is no interaction between the probe and VBC protein, and if there is a dramatic increase in fluorescence polarization value upon the addition of VBC protein, it means an interaction between them occurs to form a complex.

In analogy to the procedure as described above, the binding of HIF-1 peptide with VBC protein and its characteristics were investigated using F-HyP564 and F-HyP402 fluorescent probes containing hydroxyproline prepared in the above step 1) and F-P564 and F-P402 fluorescent probes not containing hydroxyproline.

To observe proline-hydroxylation dependent HIF-1 peptide-VBC protein binding, each of F-P564 and F-HyP564 was reacted with VBC protein at 25° C., followed by measurement of fluorescence polarization. As a result, the fluorescence polarization value of the reactant of F-P564 peptide and VBC protein was similar to that of F-P564 peptide itself, while the fluorescence polarization value of the reactant of F-HyP564 peptide and VBC protein was remarkably increased, compared with that of F-P564 itself. From the result, it was confirmed that Hydroxyproline containing HIF-1 peptide is bound to VBC protein and their interaction is easily detected by observing the changes of fluorescence polarization (see FIG. 1).

In addition, F-HyP564 peptide was reacted with VBC protein with increasing VBC concentrations. As a result, as expected, fluorescence polarization values of the reactant were increased VBC concentration dependently (see FIG. 2$a$), indicating that the interaction between F-HyP564 peptide and VBC protein increases VBC concentration dependently. The binding constant between F-HyP564 peptide and VBC protein was determined to be 138.1 nM (see FIG. 2$b$).

To further confirm the interaction, F-HyP402 peptide fluorescent probe was prepared from the 402$^{nd}$ proline being known as one of proline hydroxylation regions, and the experiment was performed by the same manner as described hereinbefore. As a result, fluorescence polarization value of the reactant of F-HyP402 peptide and VBC protein was increased VBC concentration dependently (see FIG. 3a), indicating that the interaction between F-HyP402 peptide and VBC protein increases VBC concentration dependently. The binding constant was determined to be 337.79 nM (see FIG. 3b). Accordingly was confirmed that proline hydroxylation in the 564$^{th}$ induces the binding with VBC protein more strongly than that in 402$^{nd}$ does.

It was confirmed from the above results that the method of the present invention enables quantitative analysis of the interaction between HIF-1 peptide containing hydroxyproline and VBC protein to form a complex by using fluorescence polarization without requirement of separation of the complex.

The present invention also provides a method for screening an inhibitor of the interaction between hydroxyproline containing HIF-1 peptide and VBC protein based on the above analytical method.

In this screening method, a candidate for an interaction inhibitor was added to the reaction solution having hydroxyproline containing HIF-1 peptide fluorescent probe and VBC protein, then the changes of fluorescence polarization values were measured. It was analogized with the decrease of fluorescence polarization value of the reactant of hydroxyproline containing HIF-1 peptide and VBC protein by the addition of a candidate for an inhibitor that the candidate worked as an inhibitor for the interaction by competing with HIF-1 peptide for being bound to VBC protein.

To test the possibility of screening an inhibitor intervening the formation of F-HyP564 peptide-VBC protein complex by taking advantage of the competence of a candidate with HIF-1 peptide, fluorescence polarization values were measured with increasing the concentration of HyP564 peptide in the reaction solution containing F-HyP564 peptide and VBC protein. As a result, F-Hyp564 peptide competed with HyP564 peptide for being bound to VBC protein. So, the formation of F-HyP564 peptide-VBC protein complex was decreased, showing reduced fluorescence polarization value, with the increase of the formation of HyP564 peptide-VBC protein complex (see FIGS. 4a and 4b). Therefore, an inhibitor of the HIF-1 peptide-VBC protein binding can be easily screened by using the above competitive action for the method for analysis of fluorescence polarization of the invention.

The present invention further provides a method for analysis of the activity of prolyl hydroxylase by using the method for analysis of fluorescence polarization of the invention.

Prolyl hydroxylase is an enzyme that induces hydroxylation of a specific proline group in HIF-1. And the method for analysis of the activity of prolyl hydroxylase using the method for analysis of fluorescence polarization is to examine whether the treatment of the enzyme to HIF-1 peptide can induce hydroxylation of a specific praline group to form a complex with VBC protein.

Prolyl hydroxylase was added to hydroxyproline-not-containing F-P564 peptide, then the mass analysis was performed with the enzyme treated reactant, F-P564 and F-HyP564 peptides. As a result, the 564$^{th}$ proline group in F-P564 was hydroxylated by the addition of prolyl hydroxylase (see FIG. 6a). F-P564, F-HyP564 and the enzyme treated reactant were respectively reacted with VBC protein to investigate the interaction between the reactant and VBC protein by using fluorescence polarization assay, followed by measurement of fluorescence polarization values of each. As a result, the fluorescence polarization value of the enzyme treated reactant was increased, eventually approaching the level close to the value of F-HyP564 peptide (see FIG. 6b), and further was confirmed that F-P564 peptide was converted into F-HyP564 peptide with the activation of prolyl hydroxylase, leading to the formation of a complex with VBC protein, and such interaction could be quantitatively analyzed by the method of the invention based on the observation of fluorescence polarization values.

By the method of the invention for quantitative analysis of the interaction between HIF-1 peptide and VBC protein using fluorescence polarization, the binding of hydroxyproline containing HIF-1 peptide with VBC protein can be quantitatively analyzed, an inhibitor for HIF-1-VBC protein bond can be easily screened, and the activity of prolyl hydroxylase can be simply measured. In addition, the method of the invention has such advantages that the separation of HIF-1-VBC protein complex is not necessary, making the procedure simple and high-speed screening is possible by using a well plate.

MODE FOR INVENTION

Figure 1:
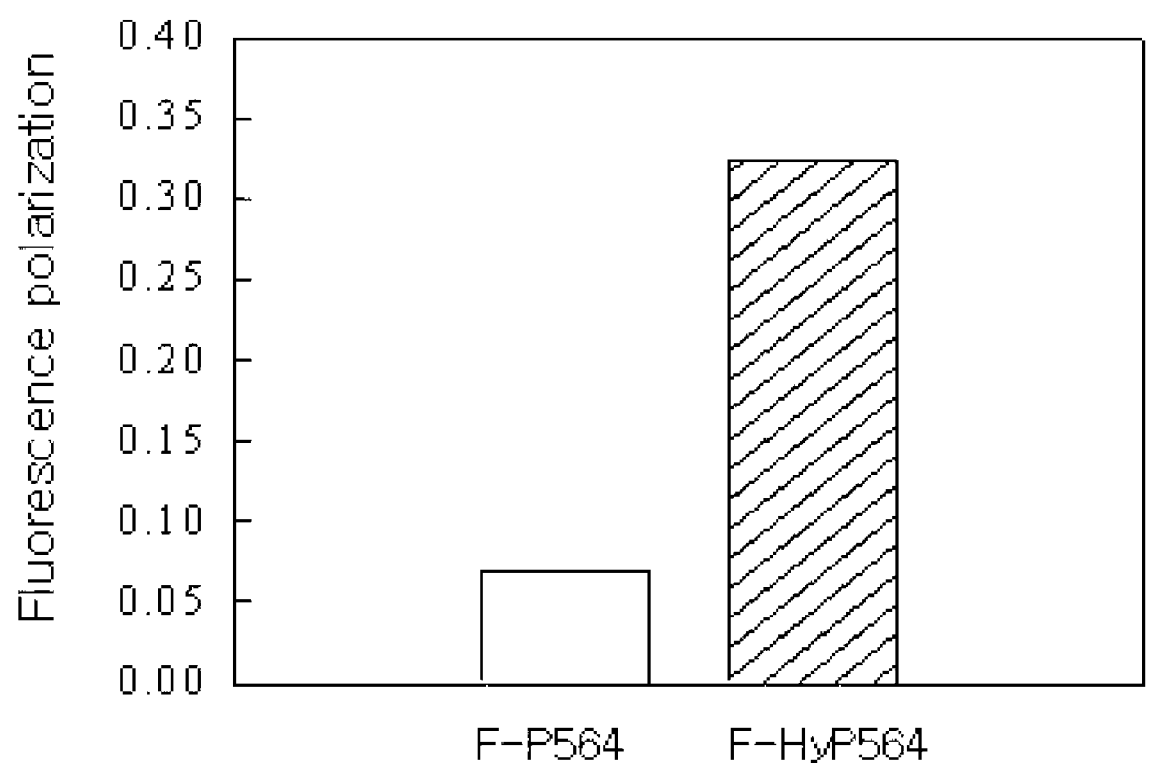
FIG. 1 is a graph showing the fluorescence polarization changes measured after the reaction of F-P564 and F-HyP564 respectively with VBC protein to investigate the formation of a complex.

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXAMPLE 1

Preparation of VBC Protein

Human von Hippel-Lindau gene fragment (corresponding to 54~213 a.a. region of the amino acid sequence represented by GenBank Accession No: NM000551) and human Elongin B fragment (corresponding to 1~118 a.a. region of the amino acid sequence represented by GenBank Accession No: NM007108) were inserted into a modified pGEX-4T-1, resulting in plasmid pGEX4T-VHL-EB. Likewise, human Elongin C fragment (corresponding to 17~112 a.a. region of the amino acid sequence represented by GenBank Accession No: NM005648) was inserted into pET29b vector, resulting in plasmid PDEV-EC (Novagen). The plasmids were co-expressed massively in E. coli BL21 (DE3) (Novagen).

The transformed cells were inoculated to LB medium containing 50 µg/ml of ampicillin at 37° C., and then cultured until OD reached 0.8~0.9. The expression was induced with 0.5 mM IPTG (isopropyl-β-D-thiogalactopyranoside), followed by further culture at 18° C. for 15 hours. PMSF (phenylmethylsulfonyl fluoride) and lysozyme were added to 10 mM phosphate based saline buffer (PBS, pH 7.4, 110 mM NaCl and 1 mM DTT [dithiotheitol]) at the final concentration of 0.2 mM and 1 mg/ml. Cells were recovered by centrifugation, which were suspended in the above buffer solution and lysated at 4° C. by ultrasonification. 2% Triton X-100 was added to the cell extract, and stirred, which was then put in ice for 10 minutes, followed by centrifugation for 30 minutes at 13,000 rpm. Supernatant was separated, to which 1 mM DTT was added. Glutathione-sepharose 4B resin (Amersham Bioscience) was added thereto, followed by stirring for 2 hours at 4° C. Phosphate buffer was added to the reacted resin mixture by 10-fold volume, followed by centrifugation for 5 minutes at 2,100 rpm to eliminate supernatant. The above experiment processes were repeated three times to eliminate non-reacted supernatant.

The reacted resin mixture was put in Bio-Spin® Disposable Chromatography Columns (Bio-Rad), filtered by 5 ml PBS, and filtered again by 2 ml of 1 M NaCl solution to eliminate unnecessary reactants. The column was eluted by 10 mM glutathione (GSH) to recover GST-VBC protein. The collected protein was confirmed by SDS-PAGE and quantified by BCA protein assay (Pierce).

EXAMPLE 2

Analysis of the Binding Capacity of Fluorescent Labeled HIF-1 Peptide to VBC Protein <2-1> Preparation of Fluorescent Labeled HIF-1 Peptide To prepare HIF-1α (hypoxia-inducible factor) fluorescent probe, the $556^{th}$-$575^{th}$ amino acid region and the $390^{th}$-$417^{th}$ amino acid region of HIF-1α were selected for the binding with VBC protein (Min J. H. et al., Science 296: 1886-1889, 2002). Aminocaproic acid linker was conjugated to N-terminal of the selected region and the very end was tagged with FITC (fluorescein isothiocyanate), resulting in the synthesis of a target peptide (Anygen, Korea). The synthesized fluorescent probes were named 'F-P564' and 'F-P402' and they were confirmed to have amino acid sequences represented by SEQ ID NO:1 and SEQ ID NO:2, respectively. In addition, the $564^{th}$ proline (the $12^{th}$ amino acid of SEQ ID NO: 1) of F-P564 and the $402^{nd}$ proline (the $16^{th}$ amino acid of SEQ ID NO:2) of F-P402 were synthesized to yield hydroxyproline-containing F-HyP564 and F-hyP402 (Anygen, Korea), which have amino acid sequences respectively represented by SEQ ID NO:3 and SEQ ID NO:4.

Fluorescence polarization changes were measured during the formation of protein-ligand complex of VBC protein and the above peptides prepared in Example 1, to investigate binding capacity and characteristics thereof. Fluorescence polarization was measured by using fluorometer (Perkin-Elmer), and the size of slit was 5 nm and integration time was 5 seconds. A buffer solution containing 50 mM Tris and 120 mM NaCl, pH 8.0, was supplemented with NP-40 (nonidet P40) by 0.5%, for being utilized for the experiments of binding and interaction.

<2-2> Analysis of the Binding Capacity of Fluorescent Labeled HIF-1 Peptide to VBC Protein To further confirm the binding of the fluorescent probe synthesized in the above Example <2-1> with VBC protein by using fluorescence polarization, F-P564 peptide and F-HyP54 peptide were dissolved in the buffer solution respectively at the concentration of 100 nM, to which 800 nM of VBC protein was added and mixed at 25° C. After mixing, fluorescence polarization was measured. As a result, fluorescence polarization value of hydroxyproline-not containing F-P564 was 0.066, while fluorescence polarization value of hydroxyproline containing F-HyP564 peptide was increased to 0.324 (FIG. 1). The results indicate that fluorescence polarization is increased greatly by the interaction between hydroxyproline containing HIF-1 peptide and VBC protein having high molecular weight to form a complex, and such binding for being a complex can be easily detected by measuring the changes of fluorescence polarization.

Figure 2A:
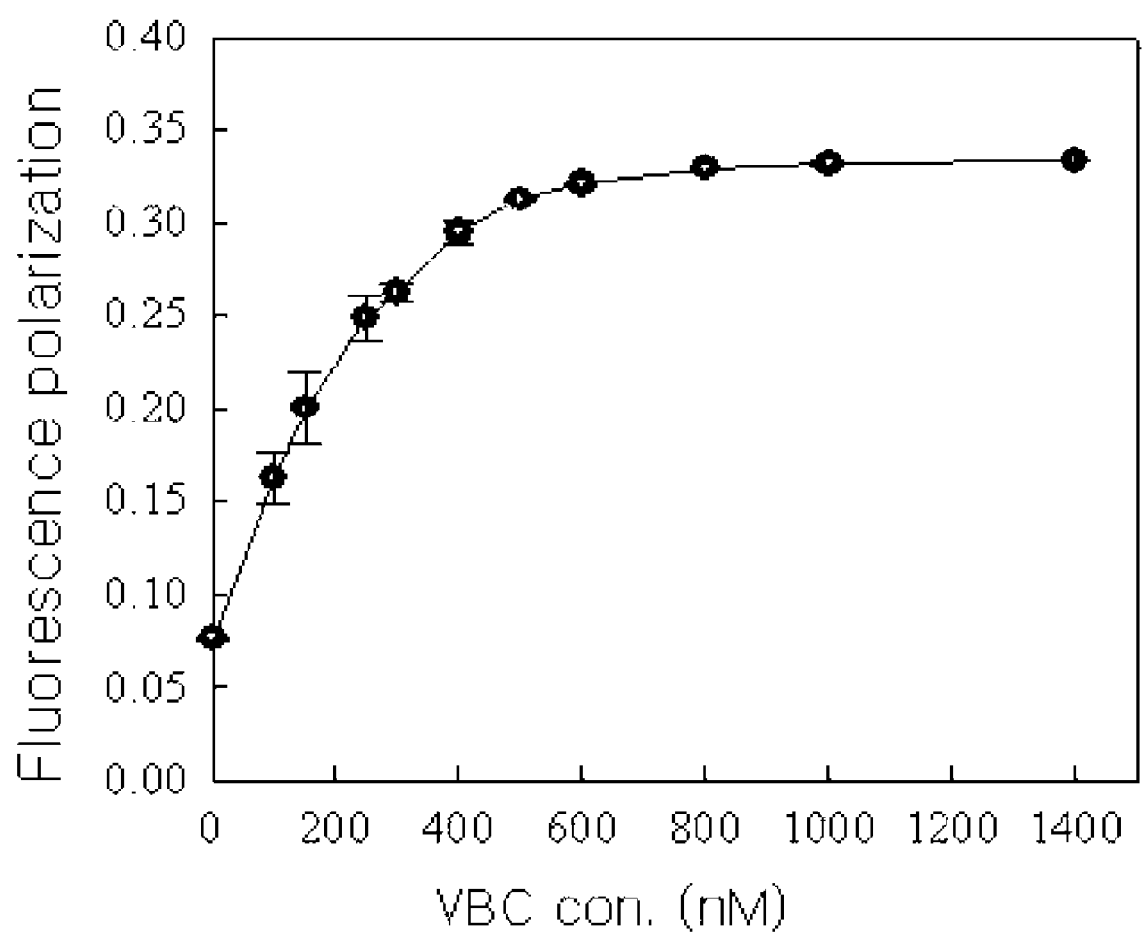
FIG. 2a is a graph showing the fluorescence polarization changes measured with increasing VBC concentration in F-HyP564 peptide to investigate the formation of a complex.
Figure 2B:
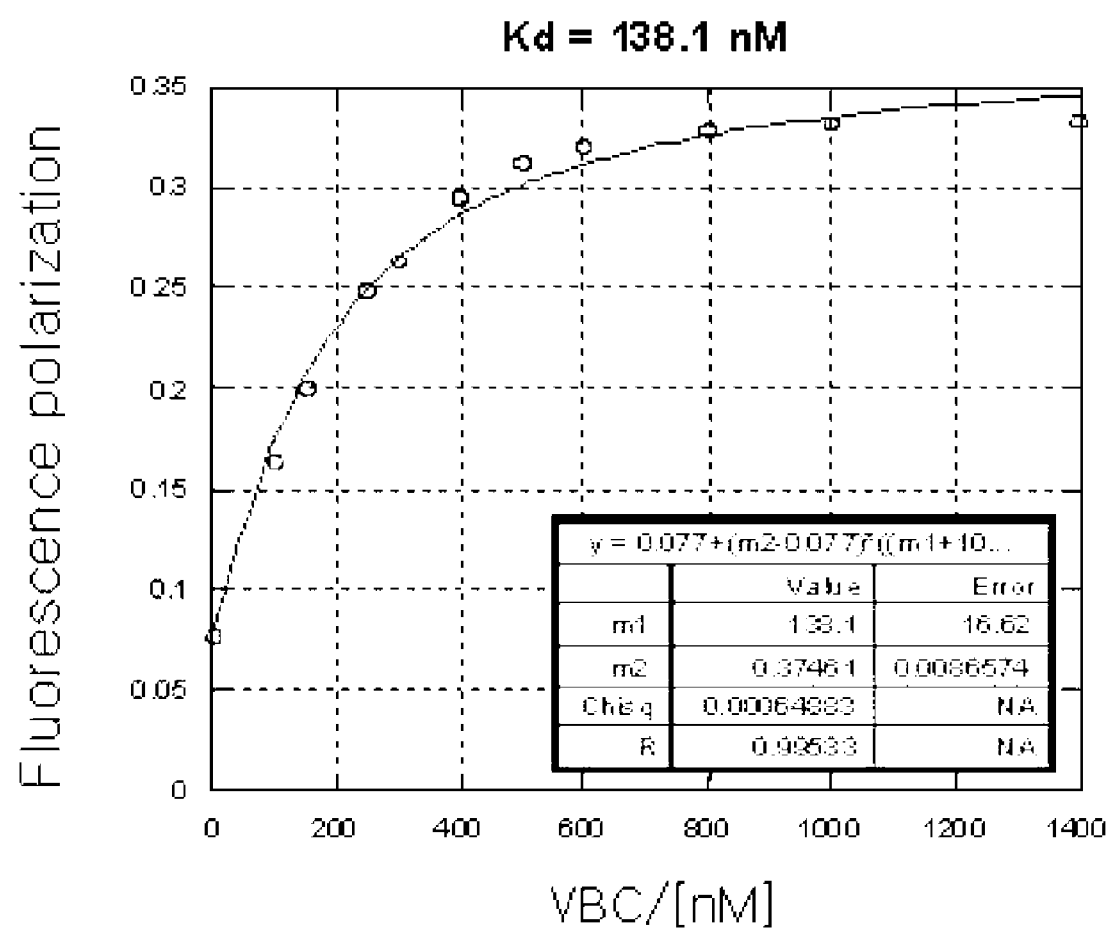
FIG. 2b is a graph showing the binding constants of F-HyP564-VBC protein bond formed in FIG. 2a, analyzed by KaleidaGraph program.

<2-3> VBC Concentration Dependent Binding of Fluorescent Labeled HIF-1 Peptide with VBC Protein F-HyP564 peptide was reacted with VBC protein with increasing VBC concentration from 0 to 1400 nM in the same manner as described in Example <2-2>, followed by measuring the changes of fluorescence polarization. As a result, fluorescence polarization was increased in proportion to the concentration of VBC protein, suggesting that the formation of F-HyP5654 peptide-VBC protein complex is increased with the increase of VBC protein concentration (FIG. 2a).

Figure 3A:
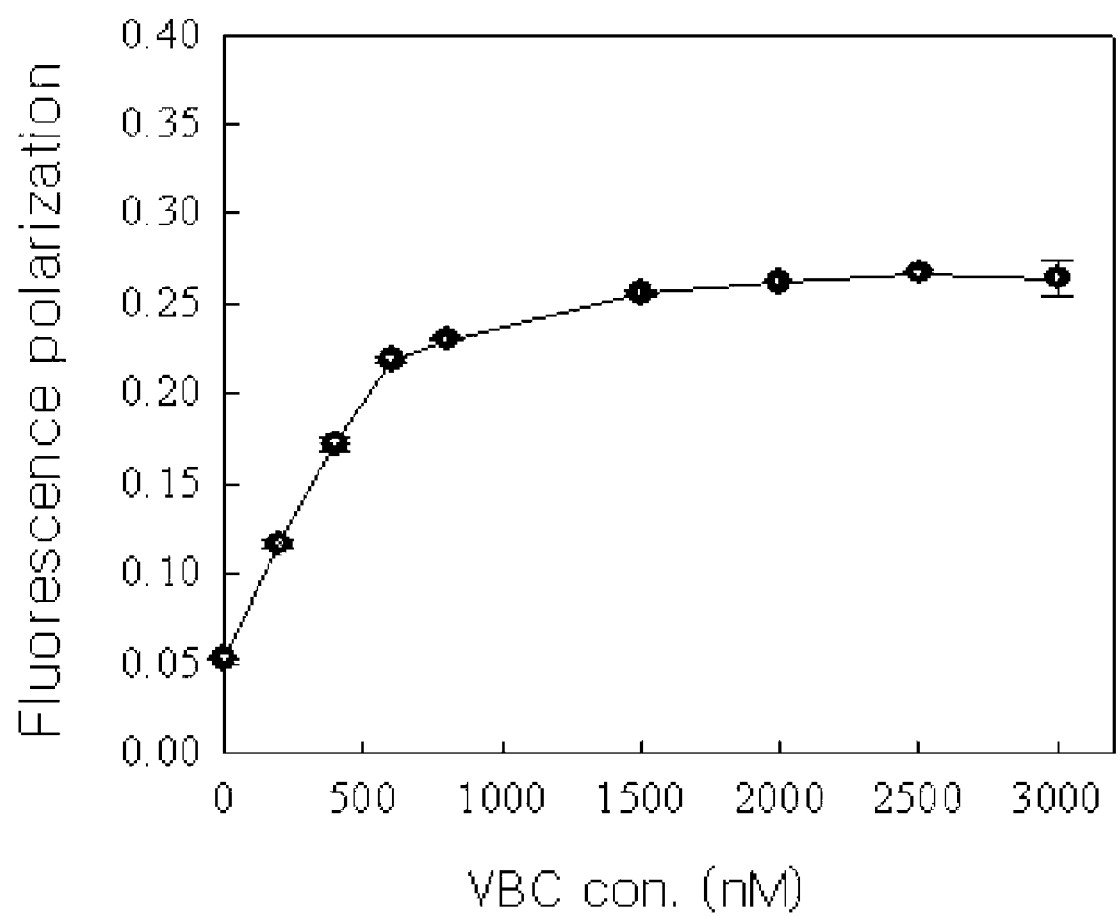
FIG. 3a is a graph showing the fluorescence polarization changes measured with increasing VBC concentration in F-HyP402 peptide to investigate the formation of a complex.
Figure 3B:
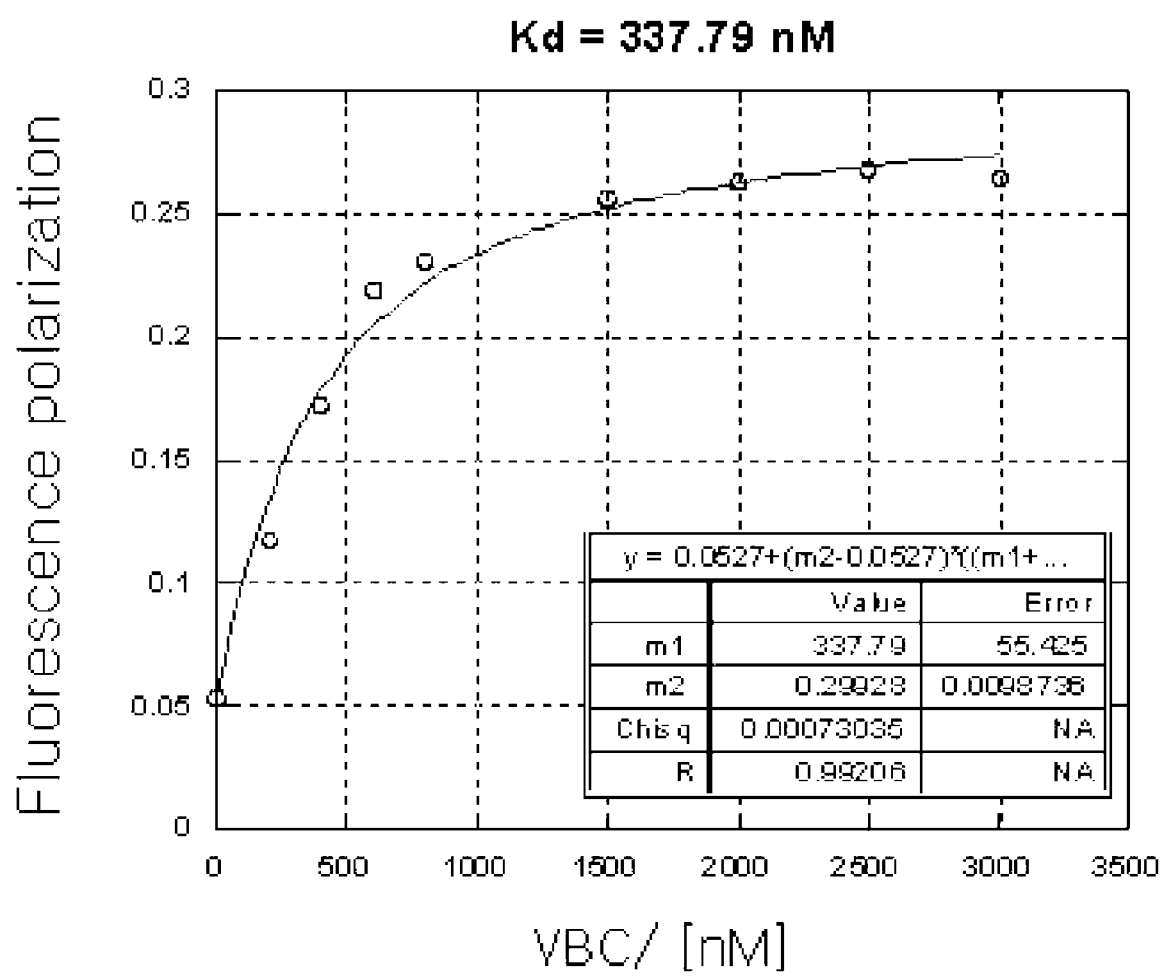
FIG. 3b is a graph showing the binding constants of F-HyP402-VBC bond formed in FIG. 3a, analyzed by KaleidaGraph program.

KaleidaGraph program was used to calculate the binding constants of F-HyP564 peptide-VBC protein according to the below reaction formulas 1 and 2. As a result, the binding constant of F-HyP564 peptide-VBC protein was determined to be 138.1 nM (FIG. 3b).

Reaction Formula 1

FP: fluorescence polarization of sample, $FP_0$: fluorescence polarization as [VBC]=0, $FP_{max}$: fluorescence polarization when all the F-HyP564 peptides were bound to VBC protein, forming a complex, $[VBC]_0$: VBC concentration in sample, $[F\text{-}HyP564]_0$: F-HyP564 peptide concentration in sample, $K_d$: the binding constant of the complex of VBC protein and F-HyP564 peptide Reaction Formula 2

[HyP564]: HyP564 peptide concentration in sample, $K_D$: the binding constant of the complex of VBC protein and HyP564 peptide F-HyP402, in which the 402$^{nd}$ proline is hydroxylated, was reacted with VBC protein with increasing VBC concentration by the same manner as the above, followed by measurement of fluorescence polarization changes. As a result, fluorescence polarization of F-HyP402 was increased VBC concentration dependently (FIG. 3a). The binding constant of the protein complex was calculated by KaleidaGraph program according to reaction formulas 1 and 2, and the binding constant was determined to be 337.79 nM (FIG. 3b).

The above results indicate that proline hydroxylation in the 564$^{th}$ amino acid of HIF-1 induces more strong interaction with VBC than proline hydroxylation in the 402$^{nd}$, and the interaction between the two proteins can be simply detected by measuring fluorescence polarization.

EXAMPLE 3

Screening of an Inhibitor of F-HyP564 Peptide-VBC Protein Binding

In order to confirm whether the established method using fluorescence polarization of the invention could be successfully used for the screening of an inhibitor of F-HyP564 peptide-VBC protein binding which works by competing with F-HyP564 peptide for being bound to VBC protein, HyP564 which was not labeled with a fluorescein was used as an inhibitor for following experiments.

Figure 4A:
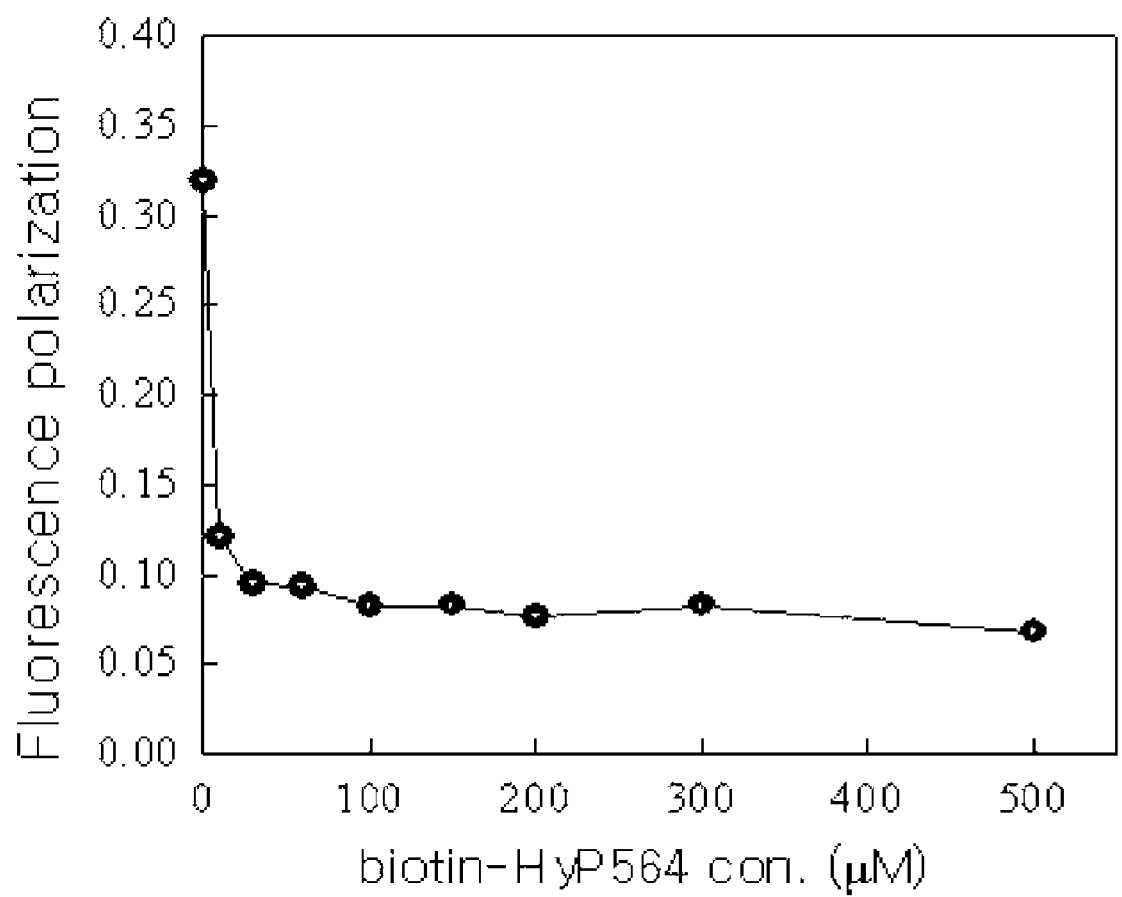
FIG. 4a is a graph showing the fluorescence polarization changes measured after the addition of a candidate for an inhibitor of the bond formation to the reactant of F-HyP564 peptide and VBC protein to investigate the formation of a complex.
Figure 4B:
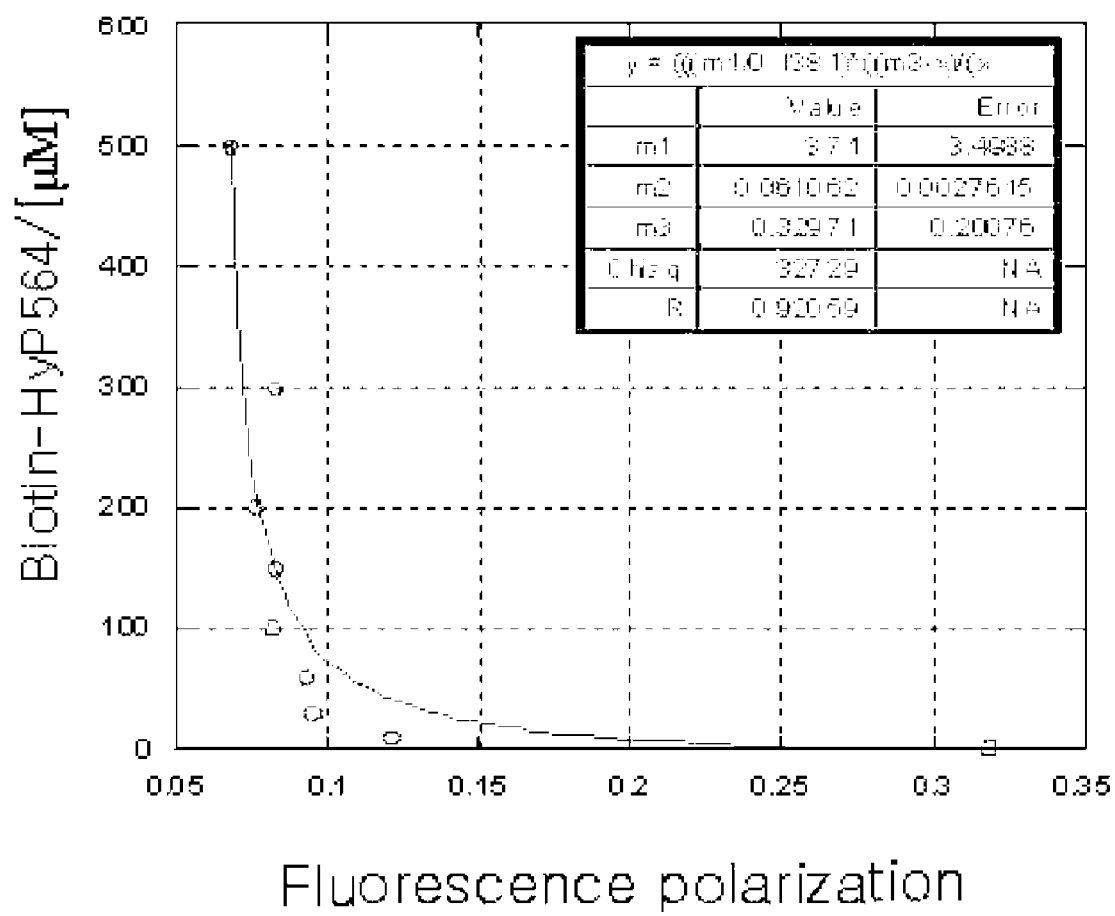
FIG. 4b is a graph showing the 50% inhibition concentration of HyP564, confirmed as an inhibitor in FIG. 4a, confirmed by KaleidaFraph program.

100 nM of F-HyP564 peptide and 500 nM of VBC protein were dissolved in the same buffer solution as used in the above Example 2, to which HyP564 peptide was added with increasing its concentration from 0 to 500 nM and mixed at 25° C. Fluorescence polarization of the reaction solution was measured. As a result, fluorescence polarization was decreased with the addition of HyP5654 peptide (FIG. 4a), and the binding constant of the complex of HyP564 peptide-VBC protein was determined to be 3.71 μM (FIG. 4b).

The results indicate that HyP564 peptide competes with F-HyP564 peptide for being bound to VBC protein, so that the increase of HyP564 peptide-VBC protein binding means the decrease of F-HyP564 peptide-VBC protein binding, which provides an idea for screening an inhibitor of the interaction between HIF-1 and VBC protein.

EXAMPLE 4

Investigation of Crucial Regions for the Binding of F-HyP564 Peptide with VBC Protein To confirm a region of F-HyP564 peptide that is specifically bound to VBC protein, Hy-N fragment peptide (amino acid sequence: ALAHyPYIPA) (SEQ ID NO:9) was synthesized in which N fragment (amino acid sequence: ALAPYIPA) (SEQ ID NO:10) and C fragment (amino acid sequence: DDDFQLR) (SEQ ID NO:11) and proline in N fragment of amino acid sequence represented by SEQ ID NO:1 were hydroxylated (Anygen, Korea).

Reaction solution containing 100 nM of F-HyP564 peptide and 500 nM of VBC protein was prepared under the same conditions as described above in Example <2-2>, to which P564 peptide, N, C and Hy-N fragments were added with increasing their concentrations from 0 to 500 μM. After mixing, fluorescence polarization changes were measured.

Figure 5A:
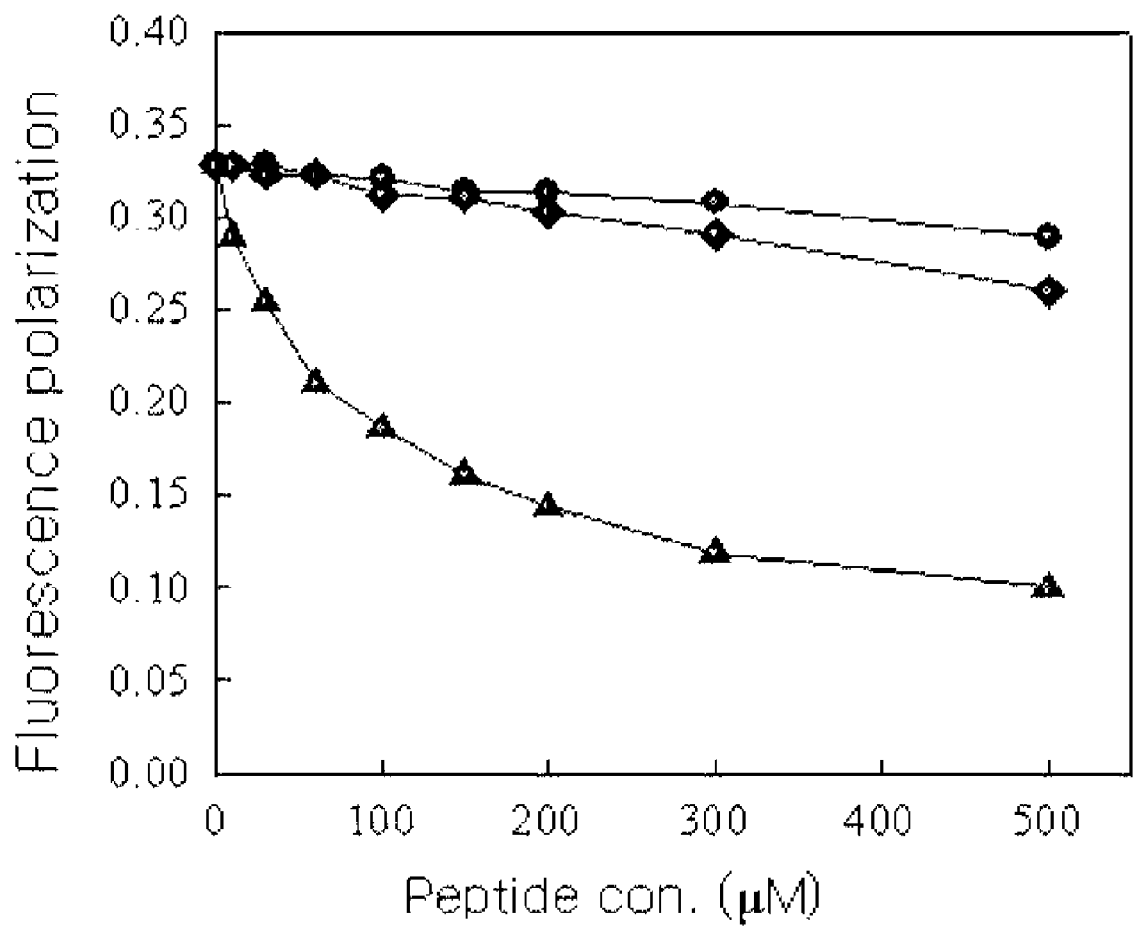
FIG. 5a is a graph showing the fluorescence polarization changes measured after the addition of various HyP564 peptide fragments as inhibitors to the reactant of F-HyP564 peptide and VBC protein to investigate the binding region.
Figure 5B:
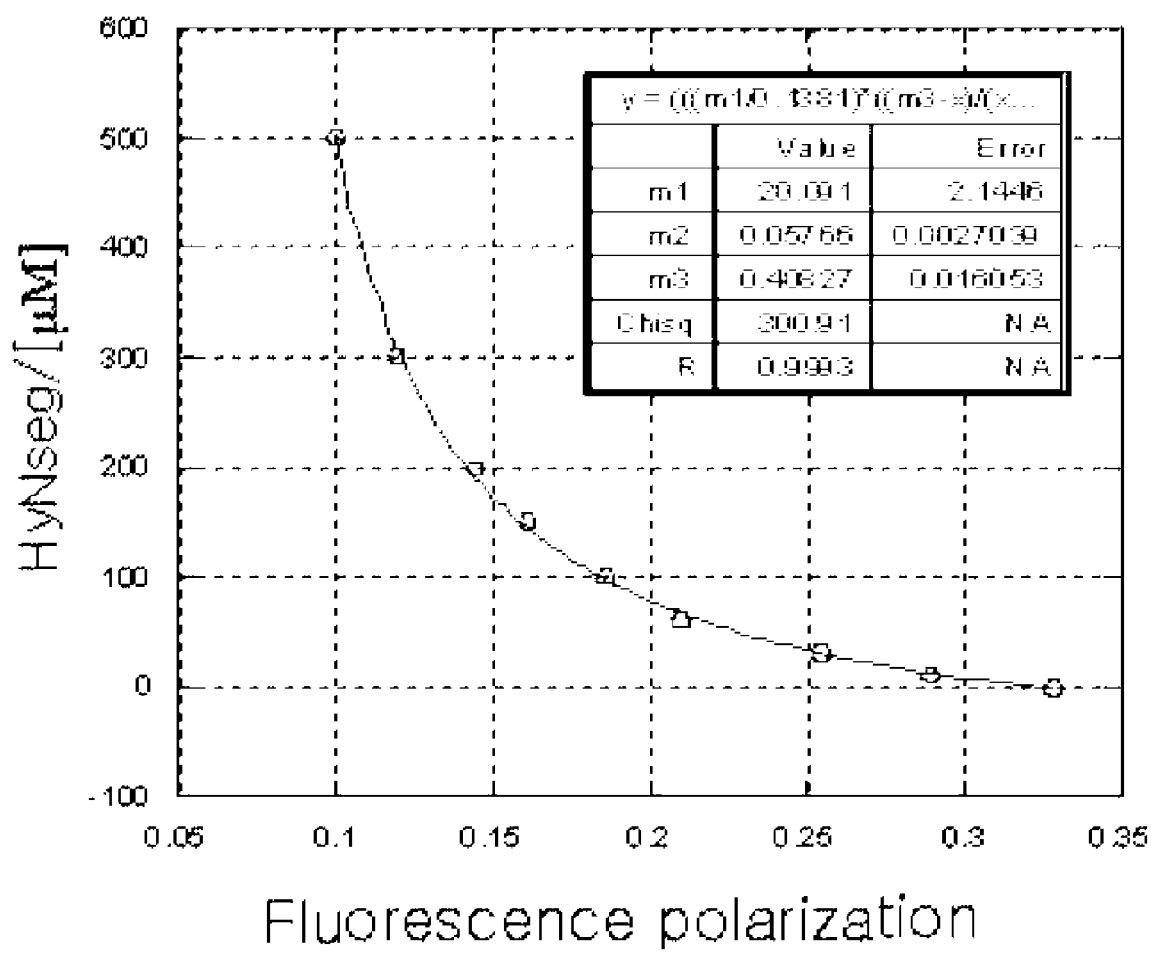
FIG. 5b is a graph showing the 50% inhibition concentration of N-fragment of HyP564 peptide showing inhibiting effect, measured by KaleidaGraph program.

As shown in FIG. 5a, only a slight decrease of fluorescence polarization was detected in the sample containing P564 peptide and N and C fragments when the peptide concentration was high, suggesting that competition of an inhibitor did not significantly affect the binding of HyP564 peptide with VBC protein. On the other hand, fluorescence polarization in the sample containing Hy-N fragment was remarkably decreased with the increase of peptide concentration, and the inhibitory effect of the peptide on the binding was quantitatively measured by KaleidaGraph program using reaction formulas 1 and 2, resulting in the determining the binding constant to be 20 μM (FIG. 5b).

From the above results, it was confirmed that a crucial region involved in the interaction between F-HyP564 peptide and VBC protein is the region harboring hydroxyproline group.

EXAMPLE 5

Analysis of Prolyl Hydroxylase Activity by the Measurement of Fluorescence Polarization F-P564 peptide was treated with HIF-1α specific prolyl-4-hydroxylase-2 (PHD-2), known as an enzyme specifically inducing hydroxylation in a specific proline group of HIF-1α, then fluorescence polarization was measured to investigate the binding of the peptide with VBC protein.

At first, human PHD2 gene (GenBank Accession No: AJ310543) cloned from human lymphocyte cDNA library was cloned into pET21b vector (Novagen), resulting in the construction of plasmid pET21b-PHD2. The plasmid was mass-expressed in $E.\ coli$. PHD2 protein which was mass-expressed in the above $E.\ coli$ transformant was purified by Ni-affinity chromatography and gel-filtration using histidine-tag. Finally, prolyl hydroxylase was concentrated by ultracentrifugation and used for further experiments.

Figure 6A:
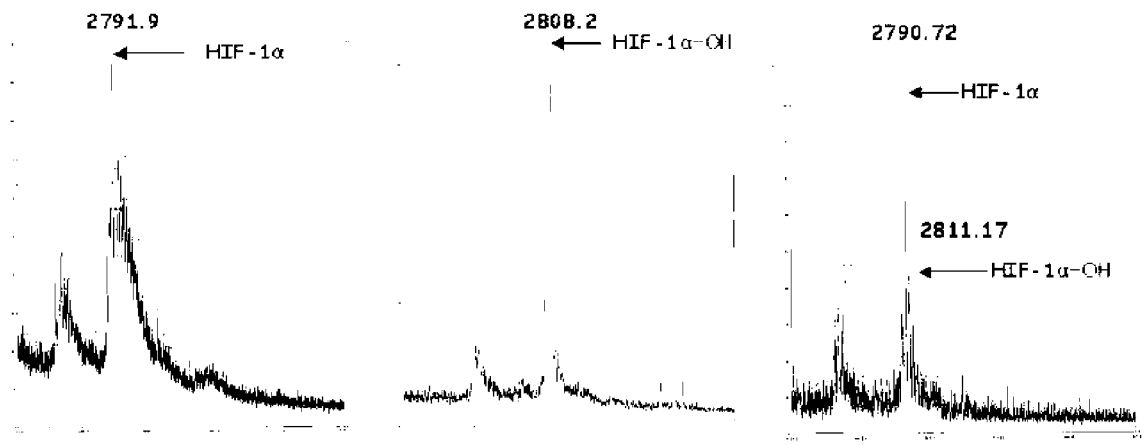
FIG. 6a is a set of graphs showing the prolyl hydroxylase-induced hydroxylation in F-P564 peptide, confirmed by mass spectrometry.

To analyze prolyl hydroxylation, ascorbic acid (final conc. 2 mM), α-ketoglutarate (final conc. 5 mM) and iron (II) chloride hydrate (final conc. 100 μM) were added to the buffer solution (20 mM Tris-HCl, pH 8.0, 100 mM NaCl, 1 mM EDTA, 1 mM PMSF, 0.5% NP-40). 4 μg of proline hydroxylase and 16 μM of F-P564 peptide were mixed, and added to the prepared buffer solution, followed by reaction for 90 minutes at 30° C. Upon completion of the reaction, F-P564, F-HyP564 and enzyme reactant were quantified with mass-spectrometry to confirm proline hydroxylation in F-P564 peptide (FIG. 6a).

Figure 6B:
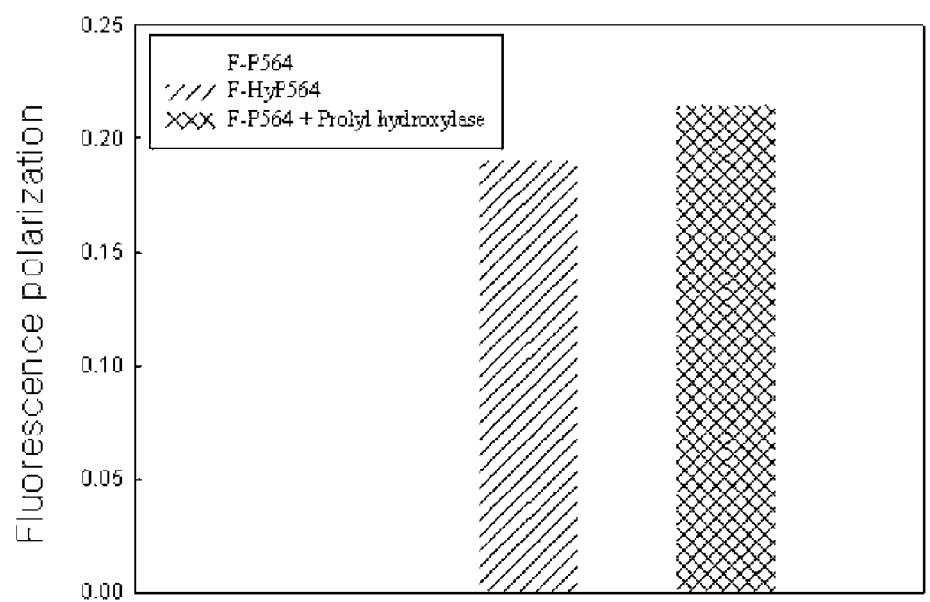
FIG. 6b is a graph showing the comparison of fluorescence polarization changes during the prolyl hydroxylase-induced interaction between F-P564 peptide and VBC protein with those during the binding of F-P564 peptide or F-HyP564 peptide with VBC protein.

F-P564, F-HyP564 and enzyme reactant (F-P564: 100 nM, F-HyP564: 100 nM, enzyme reactant: 500 nM) were respectively mixed with 500 nM of VBC protein at 25° C. in the same buffer solution as prepared in Example <2-2> under the same condition as above, followed by measurement of fluorescence polarization. As a result, fluorescence polarization value of the mixture containing enzyme reactant was remarkably increased with approaching the level close to the value of the mixture containing F-HyP564 peptide, unlike the mixture containing F-P564 peptide (FIG. 6b).

The above results indicate that observation of changes of fluorescence polarization can confirm the binding of HIF-1 peptide which does not include hydroxyproline with VBC protein when a specific proline group of HIF-1 peptide is hydroxylated by prolyl hydroxylase, and further enable the analysis of the activity of prolyl hydroxylase.

Therefore, the method of the present invention provides ways of analyzing quantitatively the binding of hydroxyproline containing fluorescent peptide probe with VBC protein and screening an inhibitor of HIF-1-VBC bond as well as measuring the activity of prolyl hydroxylase.

INDUSTRIAL APPLICABILITY

As explained hereinbefore, the method of the present invention for quantitative analysis of binding of HIF-1 peptide with VBC protein by using fluorescence polarization is carried out simply measuring the changes of fluorescence polarization without separation process of HIF-1-VBC protein complex. Thus, the method of the invention for quantitative analysis of the binding of HIF-1 peptide and VBC protein can be also effectively used for screening an inhibitor of the interaction between HIF-1 peptide and VBC protein and analyzing the activity of prolyl hydroxylase.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A method for quantitative analysis of proline hydroxylation-induced interaction between HIF-1 peptide and VBC protein using fluorescence polarization, comprising the following steps:
   1) preparing a fluorescent probe by attaching a fluorescein to hydroxyproline containing HIF-1 peptide selected from the group consisting of SEQ ID NO: 3 and SEQ ID NO: 4;
   2) reacting the fluorescent probe with VBC protein; and
   3) measuring the fluorescence polarization of the above reactant; and
   4) comparing the fluorescence polarization measured in step 3) with fluorescence polarization measured with fluorescence probe alone to investigate the changes of fluorescent polarization.

2. The method as set forth in claim 1, wherein the fluorescein is selected from a group consisting of fluorescein carboxylic acid (FCA), fluorescein isothiocyanate (FITC), fluorescein thiourea (FTH), 7-acetoxycoumarin-3-yl, fluorescein-5-yl, fluorescein-6-yl, 2',7'-dichlorofluroescein-5-yl, 2',7'-dichlorofluroescein-6-yl, dihydrotetramethylrosamine -4-yl, tetramethylrhodamine-5-yl, tetrametylfhodamine-6-yl, 4,4-difluoro-5,7-dimethyl-4-bora-3a,4a-diaza-s-indacene-3-ethyl and 4,4-difluoro-5,7-diphenyl-4-bora-3a,4a-diaza-s-indacene-3-ethyl.

3. The method as set forth in claim 1, wherein the fluorescein labeled HIF-1 peptide and VBC protein are mixed in buffer solution at the ratio of 1:1-1:14 at 25°C.

4. The method as set forth in claim 1, comprising confirming binding of the fluorescent probe and VBC protein by detecting an increase of fluorescence polarization of the reactant of step 2), as measured in step 3), compared with fluorescence polarization measured with fluorescence probe alone.

5. A method for screening an inhibitor of the interaction between hydroxyproline containing HIF-1 peptide and VBC protein using the method of claim 1.

6. The method as set forth in claim 5, comprising the following steps:
   1) adding an inhibitor candidate to a reaction solution containing hydroxyproline containing fluorescent HIF-1 peptide and VBC protein for reaction;
   2) measuring the changes of fluorescence polarization of the reaction solution before and after addition of the inhibitor candidate; and
   3) determining the candidate as an inhibitor by the decrease of fluorescence polarization of the reactant of hydroxyproline containing HIF-1 peptide and VBC protein after addition of the inhibitor candidate.

7. A method for analyzing prolyl hydroxylase activity in a sample comprising:
   1) preparing a fluorescent probe by attaching a fluorescein to a HIF-1 peptide selected from the group consisting of SEQ ID NO: 1 and SEQ ID NO: 2;
   2) treating the fluorescent probe with a sample containing prolyl hydroxylase to provide a reaction sample;
   3) reacting the reaction sample of step 2) with VBC protein and measuring fluorescence polarization thereof; and
   4) comparing fluorescence polarization measured in step 3) with fluorescence polarization measured with fluorescence probe alone, wherein a difference in fluorescence polarization indicates prolyl hydroxylase activity.

8. The method as set forth in claim 7, wherein the fluorescein is selected from a group consisting of fluorescein carboxylic acid (FCA), fluorescein isothiocyanate (FITC), fluorescein thiourea (FTH), 7-acetoxycoumarin-3-yl, fluorescein-5-yl, fluorescein-6-yl, 2',7'-dichloro fluorescein-5-yl, 2',7'-dichloro fluorescein-6-yl, dihydrotetramethylrosamine-4-yl, tetramethylrhodamine-5-yl, tetramethylrhodamine-6-yl, 4,4-difluoro-5,7-dimethyl-4-bora -3a,4a-diaza-s-indacene-3-ethyl and 4,4-difluoro-5,7-diphenyl-4-bora-3a,4a-diaza-s-indacene-3-ethyl.

9. The method as set forth in claim 7, wherein the fluorescent probe or the hydroxyproline containing fluorescein-labeled HIF-1 peptide and the VBC protein are mixed in buffer solution at the ratio of 1:1-1:14 at 25°C.

* * * * *

SEQUENCE LISTING

```
<160> NUMBER OF SEQ ID NOS: 11

<210> SEQ ID NO 1
<211> LENGTH: 23
<212> TYPE: PRT
<213> ORGANISM: Artificial Sequence
<220> FEATURE:
<223> OTHER INFORMATION: FITC labeled HIF-1 peptide F-P564

<400> SEQUENCE: 1

Ala Cys Ala Asp Leu Asp Leu Glu Ala Leu Ala Pro Tyr Ile Pro Ala
1               5                   10                  15

Asp Asp Asp Phe Gln Leu Arg
            20

<210> SEQ ID NO 2
<211> LENGTH: 31
<212> TYPE: PRT
<213> ORGANISM: Artificial Sequence
<220> FEATURE:
<223> OTHER INFORMATION: FITC labeled HIF-1 peptide, F-P402

<400> SEQUENCE: 2

Ala Cys Ala Leu Lys Lys Glu Pro Asp Ala Leu Thr Leu Leu Ala Pro
1               5                   10                  15

Ala Ala Gly Asp Thr Ile Ile Ser Leu Asp Phe Gly Ser Asn Asp
            20                  25                  30

<210> SEQ ID NO 3
<211> LENGTH: 23
<212> TYPE: PRT
<213> ORGANISM: Artificial Sequence
<220> FEATURE:
<223> OTHER INFORMATION: F-HyP564, Hydroxylated Pro at residue 12

<400> SEQUENCE: 3

Ala Cys Ala Asp Leu Asp Leu Glu Ala Leu Ala Pro Tyr Ile Pro Ala
1               5                   10                  15

Asp Asp Asp Phe Gln Leu Arg
            20

<210> SEQ ID NO 4
<211> LENGTH: 31
<212> TYPE: PRT
<213> ORGANISM: Artificial Sequence
<220> FEATURE:
<223> OTHER INFORMATION: F-HyP402, hydroxylated Pro at residue 16

<400> SEQUENCE: 4

Ala Cys Ala Leu Lys Lys Glu Pro Asp Ala Leu Thr Leu Leu Ala Pro
```

-continued

```
                1               5                   10                  15
Ala Ala Gly Asp Thr Ile Ile Ser Leu Asp Phe Gly Ser Asn Asp
                 20                  25                  30

<210> SEQ ID NO 5
<211> LENGTH: 826
<212> TYPE: PRT
<213> ORGANISM: Homo sapiens

<400> SEQUENCE: 5

Met Glu Gly Ala Gly Gly Ala Asn Asp Lys Lys Lys Ile Ser Ser Glu
1               5                   10                  15

Arg Arg Lys Glu Lys Ser Arg Asp Ala Ala Arg Ser Arg Arg Ser Lys
                 20                  25                  30

Glu Ser Glu Val Phe Tyr Glu Leu Ala His Gln Leu Pro Leu Pro His
             35                  40                  45

Asn Val Ser Ser His Leu Asp Lys Ala Ser Val Met Arg Leu Thr Ile
         50                  55                  60

Ser Tyr Leu Arg Val Arg Lys Leu Leu Asp Ala Gly Asp Leu Asp Ile
65                  70                  75                  80

Glu Asp Asp Met Lys Ala Gln Met Asn Cys Phe Tyr Leu Lys Ala Leu
                 85                  90                  95

Asp Gly Phe Val Met Val Leu Thr Asp Asp Gly Asp Met Ile Tyr Ile
            100                 105                 110

Ser Asp Asn Val Asn Lys Tyr Met Gly Leu Thr Gln Phe Glu Leu Thr
        115                 120                 125

Gly His Ser Val Phe Asp Phe Thr His Pro Cys Asp His Glu Glu Met
    130                 135                 140

Arg Glu Met Leu Thr His Arg Asn Gly Leu Val Lys Lys Gly Lys Glu
145                 150                 155                 160

Gln Asn Thr Gln Arg Ser Phe Phe Leu Arg Met Lys Cys Thr Leu Thr
                165                 170                 175

Ser Arg Gly Arg Thr Met Asn Ile Lys Ser Ala Thr Trp Lys Val Leu
            180                 185                 190

His Cys Thr Gly His Ile His Val Tyr Asp Thr Asn Ser Asn Gln Pro
        195                 200                 205

Gln Cys Gly Tyr Lys Lys Pro Pro Met Thr Cys Leu Val Leu Ile Cys
    210                 215                 220

Glu Pro Ile Pro His Pro Ser Asn Ile Glu Ile Pro Leu Asp Ser Lys
225                 230                 235                 240

Thr Phe Leu Ser Arg His Ser Leu Asp Met Lys Phe Ser Tyr Cys Asp
                245                 250                 255

Glu Arg Ile Thr Glu Leu Met Gly Tyr Glu Pro Glu Glu Leu Leu Gly
            260                 265                 270

Arg Ser Ile Tyr Glu Tyr Tyr His Ala Leu Asp Ser Asp His Leu Thr
        275                 280                 285

Lys Thr His His Asp Met Phe Thr Lys Gly Gln Val Thr Thr Gly Gln
    290                 295                 300

Tyr Arg Met Leu Ala Lys Arg Gly Gly Tyr Val Trp Val Glu Thr Gln
305                 310                 315                 320

Ala Thr Val Ile Tyr Asn Thr Lys Asn Ser Gln Pro Gln Cys Ile Val
                325                 330                 335

Cys Val Asn Tyr Val Val Ser Gly Ile Ile Gln His Asp Leu Ile Phe
            340                 345                 350
```

```
Ser Leu Gln Gln Thr Glu Cys Val Leu Lys Pro Val Glu Ser Ser Asp
            355                 360                 365

Met Lys Met Thr Gln Leu Phe Thr Lys Val Glu Ser Glu Asp Thr Ser
            370                 375                 380

Ser Leu Phe Asp Lys Leu Lys Lys Glu Pro Asp Ala Leu Thr Leu Leu
385                 390                 395                 400

Ala Pro Ala Ala Gly Asp Thr Ile Ile Ser Leu Asp Phe Gly Ser Asn
                405                 410                 415

Asp Thr Glu Thr Asp Asp Gln Gln Leu Glu Glu Val Pro Leu Tyr Asn
            420                 425                 430

Asp Val Met Leu Pro Ser Pro Asn Glu Lys Leu Gln Asn Ile Asn Leu
            435                 440                 445

Ala Met Ser Pro Leu Pro Thr Ala Glu Thr Pro Lys Pro Leu Arg Ser
            450                 455                 460

Ser Ala Asp Pro Ala Leu Asn Gln Glu Val Ala Leu Lys Leu Glu Pro
465                 470                 475                 480

Asn Pro Glu Ser Leu Glu Leu Ser Phe Thr Met Pro Gln Ile Gln Asp
                485                 490                 495

Gln Thr Pro Ser Pro Ser Asp Gly Ser Thr Arg Gln Ser Ser Pro Glu
            500                 505                 510

Pro Asn Ser Pro Ser Glu Tyr Cys Phe Tyr Val Asp Ser Asp Met Val
            515                 520                 525

Asn Glu Phe Lys Leu Glu Leu Val Glu Lys Leu Phe Ala Glu Asp Thr
            530                 535                 540

Glu Ala Lys Asn Pro Phe Ser Thr Gln Asp Thr Asp Leu Asp Leu Glu
545                 550                 555                 560

Met Leu Ala Pro Tyr Ile Pro Met Asp Asp Asp Phe Gln Leu Arg Ser
                565                 570                 575

Phe Asp Gln Leu Ser Pro Leu Glu Ser Ser Ser Ala Ser Pro Glu Ser
            580                 585                 590

Ala Ser Pro Gln Ser Thr Val Thr Val Phe Gln Gln Thr Gln Ile Gln
            595                 600                 605

Glu Pro Thr Ala Asn Ala Thr Thr Thr Thr Ala Thr Thr Asp Glu Leu
            610                 615                 620

Lys Thr Val Thr Lys Asp Arg Met Glu Asp Ile Lys Ile Leu Ile Ala
625                 630                 635                 640

Ser Pro Ser Pro Thr His Ile His Lys Glu Thr Thr Ser Ala Thr Ser
                645                 650                 655

Ser Pro Tyr Arg Asp Thr Gln Ser Arg Thr Ala Ser Pro Asn Arg Ala
            660                 665                 670

Gly Lys Gly Val Ile Glu Gln Thr Glu Lys Ser His Pro Arg Ser Pro
            675                 680                 685

Asn Val Leu Ser Val Ala Leu Ser Gln Arg Thr Thr Val Pro Glu Glu
            690                 695                 700

Glu Leu Asn Pro Lys Ile Leu Ala Leu Gln Asn Ala Gln Arg Lys Arg
705                 710                 715                 720

Lys Met Glu His Asp Gly Ser Leu Phe Gln Ala Val Gly Ile Gly Thr
                725                 730                 735

Leu Leu Gln Gln Pro Asp Asp His Ala Ala Thr Thr Ser Leu Ser Trp
            740                 745                 750

Lys Arg Val Lys Gly Cys Lys Ser Ser Glu Gln Asn Gly Met Glu Gln
            755                 760                 765

Lys Thr Ile Ile Leu Ile Pro Ser Asp Leu Ala Cys Arg Leu Leu Gly
```

|  | 770 |  | 775 |  | 780 |  |  |
|---|---|---|---|---|---|---|---|

Gln Ser Met Asp Glu Ser Gly Leu Pro Gln Leu Thr Ser Tyr Asp Cys
785                 790                 795                 800

Glu Val Asn Ala Pro Ile Gln Gly Ser Arg Asn Leu Leu Gln Gly Glu
            805                 810                 815

Glu Leu Leu Arg Ala Leu Asp Gln Val Asn
        820                 825

<210> SEQ ID NO 6
<211> LENGTH: 2968
<212> TYPE: DNA
<213> ORGANISM: Homo sapiens

<400> SEQUENCE: 6

```
cctcgcctcc gttacaacgg cctacggtgc tggaggatcc ttctgcgcac gcgcacagcc      60
tccggccggc tatttccgcg agcgcgttcc atcctctacc gagcgcgcgc gaagactacg     120
gaggtcgact cgggagcgcg cacgcagctc cgccccgcgt ccgacccgcg gatcccgcgg     180
cgtccggccc gggtggtctg gatcgcggag ggaatgcccc ggagggcgga gaactgggac     240
gaggccgagg taggcgcgga ggaggcaggc gtcgaagagt acggccctga agaagacggc     300
ggggaggagt cgggcgccga ggagtccggc ccggaagagt ccggcccgga ggaactgggc     360
gccgaggagg agatggaggc cgggcggccg cggcccgtgc tgcgctcggt gaactcgcgc     420
gagccctccc aggtcatctt ctgcaatcgc agtccgcgcg tcgtgctgcc cgtatggctc     480
aacttcgacg gcgagccgca gccctaccca acgctgccgc tggcacgggc cgccgcatc      540
cacagctacc gaggtcacct ttggctcttc agagatgcag ggacacacga tgggcttctg     600
gttaaccaaa ctgaattatt tgtgccatct ctcaatgttg acggacagcc tatttttgcc     660
aatatcacac tgccagtgta tactctgaaa gagcgatgcc tccaggttgt ccggagccta     720
gtcaagcctg agaattacag gagactggac atcgtcaggt cgctctacga agatctggaa     780
gaccacccaa atgtgcagaa agacctggag cggctgacac aggagcgcat tgcacatcaa     840
cggatgggag attgaagatt tctgttgaaa cttacactgt ttcatctcag cttttgatgg     900
tactgatgag tcttgatcta gatacaggac tggttccttc cttagtttca aagtgtctca     960
ttctcagagt aaaataggca ccattgctta aagaaagtt aactgacttc actaggcatt    1020
gtgatgttta ggggcaaaca tcacaaaatg taatttaatg cctgcccatt agagaagtat    1080
ttatcaggag aaggtggtgg catttttgct tcctagtaag tcaggacagc ttgtatgtaa    1140
ggaggtttgt ataagtaatt cagtgggaat tgcagcatat cgtttaattt taagaaggca    1200
ttggcatctg cttttaatgg atgtataata catccattct acatccgtag cggttggtga    1260
cttgtctgcc tcctgctttg ggaagactga ggcatccgtg aggcagggac aagtctttct    1320
cctctttgag accccagtgc ctgcacatca tgagccttca gtcagggttt gtcagaggaa    1380
caaaccaggg gacactttgt tagaaagtgc ttagaggttc tgcctctatt tttgttgggg    1440
ggtgggagag gggaccttaa aatgtgtaca gtgaacaaat gtcttaaagg gaatcatttt    1500
tgtaggaagc attttttata attttctaag tcgtgcactt tctcggtcca ctcttgttga    1560
agtgctgttt tattactgtt tctaaactag gattgacatt ctacagttgt gataatagca    1620
ttttttgtaac ttgccatccg cacagaaaat acgagaaaat ctgcatgttt gattatagta    1680
ttaatggaca aataagtttt tgctaaatgt gagtatttct gttcctttt gtaaatatgt    1740
gacattcctg attgatttgg gttttttttgt tgttgttgtt ttgttttgtt ttgttttttt    1800
```

-continued

```
gagatggagt ctcactcttg tcacccaggc tggagtgcag tggcgccatc tcggctcact      1860
gcaacctctg cctcctgggt tcacgtaatc ctcctgagta gctgggatta caggcgcctg      1920
ccaccacgct ggccaatttt tgtactttta gtagagacag tgtttcgcca tgttggccag      1980
gctggtttca aactcctgac ctcaggtgat ccgcccacct cagcctccca aaatggtggg      2040
attacaggtg tgtgggccac cgtgcctggc tgattcagca ttttttatca ggcaggacca      2100
ggtggcactt ccacctccag cctctggtcc taccaatgga ttcatggagt agcctggact      2160
gtttcatagt tttctaaatg tacaaattct tataggctag acttagattc attaactcaa      2220
attcaatgct tctatcagac tcagtttttt gtaactaata gatttttttt tccacttttg      2280
ttctactcct tccctaatag cttttttaaaa aaatctcccc agtagagaaa catttggaaa      2340
agacagaaaa ctaaaaagga agaaaaaaga tccctattag atacacttct taaatacaat      2400
cacattaaca ttttgagcta tttccttcca gccttttag ggcagatttt ggttggtttt      2460
tacatagttg agattgtact gttcatacag ttttataccc ttttcattt aactttataa      2520 cttaaatatt gctctatgtt agtataagct tttcacaaac attagtatag tctccctttt      2580
ataattaatg tttgtgggta tttcttggca tgcatcttta attccttatc ctagcctttg      2640
ggcacaattc ctgtgctcaa aaatgagagt gacggctggc atggtggctc ccgcctgtaa      2700
tcccagtact ttgggaagcc aaggtaagag gattgcttga gcccagaact tcaagatgag      2760
cctgggctca tagtgagaac ccatctatac aaaaaatttt taaaaattag catggcggca      2820
cacatctgta atcctagcta cttggcaggc tgaggtgaga agatcattgg agtttaggaa      2880
ttggaggctg cagtgagcca tgagtatgcc actgcactcc agcctggggg acagagcaag      2940
accctgcctc aaaaaaaaaa aaaaaaaa                                        2968
```

<210> SEQ ID NO 7
<211> LENGTH: 998
<212> TYPE: DNA
<213> ORGANISM: Homo sapiens

<400> SEQUENCE: 7

```
gggaacgggg cggagcgcgg ctgcgccggc gcgtcgaggg gagaggcagc agccgcgatg       60
gacgtgttcc tcatgatccg gcgccacaag accaccatct tcacggacgc caaggagtcc      120
agcacggtgt tcgaactgaa gcgcatcgtc gagggcatcc tcaagcggcc tcctgacgag      180
cagcggctgt acaaggatga ccaactcttg gatgatggca agacactggg cgagtgtggc      240
ttcaccagtc aaacagcacg gccacaggcc ccagccacag tggggctggc cttccgggca      300
gatgacacct tgaggccct gtgcatcgag ccgttttcca gcccgccaga gctgcccgat      360
gtgatgaagc cccaggactc gggaagcagt gccaatgaac aagccgtgca gtgaggaccc      420
ccaagaggcc catttccccc aataaaagag atttgggagt ctgcctggtt gctgcctctt      480
tttcccgccc ctccctggga tgggtccac tccctgtggg ctccttttgg ggcttgtgct      540
tggcagttcc tgtgctgtcc tgtctcccag atcctgagac cctggctgag aacttggccc      600
agcctgctgc ttaaaggcac catggggacc tgggttgccc tgagacccaa gccattgtta      660
gcagctagcc agccacacca accacgccag ggggaggaaa gggaaggact gggagagaca      720
caaagaccag agccagcctc agggacaaga gattccagtt ttaggccttt ctccttctaa      780
gtgcccccca cccccatagc ctgcatgtcc actcccagac gatggccaag agcagaaaca      840
caagctggag ccagtgtcct ggtttgacag catgttcaac gagggaaccc caagacggac      900
ccacacaggt ccacccacgc tgggggctgt aatcacggag ggaagtggct gccccctaa      960
```

-continued

```
cacacccttta ataaacagtc tacagaccca aaaaaaaa                              998

<210> SEQ ID NO 8
<211> LENGTH: 668
<212> TYPE: DNA
<213> ORGANISM: Homo sapiens

<400> SEQUENCE: 8
cggggacccg gctgcggtgg ctgcgggact gacgagaaac tactaaagtt cctggggaag       60
caaagtagaa tttcataaga acaaaatgga tggagaggag aaaacctatg gtggctgtga      120
aggacctgat gccatgtatg tcaaattgat atcatctgat ggccatgaat ttattgtaaa      180
aagagaacat gcattaacat caggcacgat aaaagccatg ttgagtggcc caggtcagtt      240
tgctgagaac gaaaccaatg aggtcaattt tagagagata ccttcacatg tgctatcgaa      300
agtatgcatg tattttacgt acaaggttcg ctacactaac agctccaccg agattcctga      360
attcccaatt gcacctgaaa ttgcactgga actgctgatg gctgcgaact tcttagattg      420
ttaaataaaa taaattataa taaactgtta actcttttca gtatttaata cctgtagttc      480
agttagtaac ttttcatat atagcatgtt gcctgtatgc agttgaacta tataaagttc      540
attgcaaagc agattatctt gtttttttgc atagcaatca aagttgaaat ttgtttgcta      600
catcaacaaa ttaaggacat tttcacaaac tgagaaataa acaaatatgc aattaaaaa      660 aaaaaaaa                                                              668

<210> SEQ ID NO 9
<211> LENGTH: 8
<212> TYPE: PRT
<213> ORGANISM: Artificial Sequence
<220> FEATURE:
<223> OTHER INFORMATION: N fragment of F-P564, hydroxylated Pro at
      residue 4

<400> SEQUENCE: 9

Ala Leu Ala Pro Tyr Ile Pro Ala
1               5

<210> SEQ ID NO 10
<211> LENGTH: 8
<212> TYPE: PRT
<213> ORGANISM: Artificial Sequence
<220> FEATURE:
<223> OTHER INFORMATION: N fragment of F-P564

<400> SEQUENCE: 10

Ala Leu Ala Pro Tyr Ile Pro Ala
1               5

<210> SEQ ID NO 11
<211> LENGTH: 7
<212> TYPE: PRT
<213> ORGANISM: Artificial Sequence
<220> FEATURE:
<223> OTHER INFORMATION: C fragment of F-P564

<400> SEQUENCE: 11

Asp Asp Asp Phe Gln Leu Arg
1               5
```